United States Patent [19]

Skidmore et al.

[11] Patent Number: 4,990,664
[45] Date of Patent: Feb. 5, 1991

[54] ETHANOLAMINE DERIVATIVES

[75] Inventors: Ian F. Skidmore, Welwyn; Alan Naylor, Royston; Harry Finch, Letchworth; Lawrence H. C. Lunts, Broxbourne; Ian B. Campbell, Dane End; Peter C. North, Royston, all of England

[73] Assignee: Glaxo Group Limited, London, England

[21] Appl. No.: 230,357

[22] Filed: Aug. 10, 1988

[30] Foreign Application Priority Data

Aug. 11, 1987 [GB] United Kingdom ............... 8718938

[51] Int. Cl.$^5$ ............... C07C 309/04; C07C 233/65; A61K 31/18; A61K 31/165
[52] U.S. Cl. ............................ 564/99; 564/161
[58] Field of Search ............ 564/99, 95, 80, 161; 514/605, 617

[56] References Cited

U.S. PATENT DOCUMENTS

| 3,818,101 | 6/1974 | Baile et al. | 514/598 |
| 4,137,328 | 1/1979 | Cox et al. | 564/99 |
| 4,379,166 | 4/1983 | Neustadt et al. | 424/324 |
| 4,657,929 | 4/1987 | Inoe et al. | 564/99 |

FOREIGN PATENT DOCUMENTS

| 0162576 | 11/1985 | European Pat. Off. |
| 0178919 | 4/1986 | European Pat. Off. |
| 0220054 | 4/1987 | European Pat. Off. |
| 0220878 | 5/1987 | European Pat. Off. |
| 0223410 | 5/1987 | European Pat. Off. |
| 0208873A | 6/1982 | United Kingdom |
| 2140800A | 12/1984 | United Kingdom |
| 2159151A | 11/1985 | United Kingdom |
| 2159151 | 11/1985 | United Kingdom |
| 2162842 | 2/1986 | United Kingdom |

Primary Examiner—Richard L. Raymond
Assistant Examiner—Brian Beurbenick
Attorney, Agent, or Firm—Morgan & Finnegan

[57] ABSTRACT

The invention provides compounds of the general formula $$Z-\underset{\underset{OH}{|}}{C}H\underset{\underset{}{}}{C}HNH\underset{\underset{R^2}{|}}{C}HCH_2SCH_2Y-Q \quad (I)$$

and physiologically acceptable salts and solvates thereof, wherein
Z represents the group (a) [structure: hydroxyphenyl with A substituent]

where A represents a group selected from $HOR^3-$, $R^6NH(CH_2)_p-$, $R^{10}R^{11}N-$, $R^{12}OCH_2-$, $CH_3SO_2CH_2-$ or $NCCH_2-$;
where $R^3$ is a $C_{1-3}$alkylene group,
$R^6$ is a group selected from $R^7CO-$, $R^7NHCO-$, $R^7R^8NSO_2-$ or
$R^9SO_2-$, and p is zero or 1,
$R^7$ and $R^8$ each represent a hydrogen atom or a $C_{1-3}$alkyl group,
$R^9$ is a $C_{1-3}$alkyl group,
$R^{10}$ and $R^{11}$ each represent a hydrogen atom or a $C_{1-4}$alkyl group or, when $R^{10}$ is a hydrogen atom, $R^{11}$ may also be a $C_{1-4}$alkoxycarbonyl group, and
$R^{12}$ is a $C_{1-3}$alkyl group;

(b) [structure: phenyl with $R^4$ and $R^5$ substituents]

where one of $R^4$ and $R^5$ is a hydroxy group and the other is a hydrogen or halogen atom or a hydroxy group;

(c) [structure: aniline with $A^1$ and Cl substituents]

where $A^1$ is either a chlorine atom or a $-CF_3$ group;

(d) [pyridine structure with HOCH$_2$ and HO substituents]

(e) [quinolinone structures]

X represents a bond or a $C_{1-7}$alkenylene or $C_{2-7}$alkynylene chain, and
Y represents a bond, or a $C_{1-6}$alkylene, $C_{2-6}$alkenylene or $C_{2-6}$alkynylene chain, with the proviso that the sum total of carbon atoms in X and Y is 2 to 10;
R represents a hydrogen atom or a $C_{1-3}$alkyl group;

(Abstract continued on next page.)

$R^1$ and $R^2$ each represents a hydrogen atom or a $C_{1-3}$alkyl group; with the proviso that the sum total of carbon atoms in $R^1$ and $R^2$ is not more than 4;

Q represents a pyridyl group optionally substituted by one or two substituents selected from halogen atoms or hydroxy, $C_{1-3}$alkyl or $C_{1-3}$alkoxy groups, or Q represents a phenyl group optionally substituted by one or more substituents selected from halogen atoms or the groups $C_{1-6}$alkyl, nitro, —$(CH_2)_q R^{13}$ or —$O(CH_2)_r R^{14}$, or Q represents a phenyl group substituted by an alkylenedioxy group of formula —$O(CH_2)_t O$—; where $R^{13}$ represents hydroxy, $C_{1-6}$alkoxy, cyano, —$NR^{15}R^{16}$, —$NR^{17}COR^{18}$, —$NR^{17}SO_2R^{19}$, —$COR^{20}$, —$SR^{21}$, —$SOR^{22}$ or —$SO_2R^{22}$;

$R^{14}$ represents hydroxy or $C_{1-4}$alkoxy;

$R^{15}$ and $R^{16}$ each represent a hydrogen atom or a $C_{1-4}$alkyl group or —$NR^{15}R^{16}$ forms a saturated heterocyclic amino group which has 5–7 ring members and optionally contains in the ring one or more atoms selected from —O— or —S— or a group —NH— or —N(CH$_3$)—;

$R^{17}$ represents a hydrogen atom or a $C_{1-4}$alkyl group;

$R^{18}$ represents a hydrogen atom or a $C_{1-4}$alkyl, $C_{1-4}$alkoxy, phenyl or —$NR^{15}R^{16}$ group;

$R^{19}$ represents $C_{1-4}$alkyl, phenyl or —$NR^{15}R^{16}$;

$R^{20}$ represents hydroxy, $C_{1-4}$alkoxy or —$NR^{15}R^{16}$;

$R^{21}$ represents a hydrogen atom or a $C_{1-4}$alkyl or phenyl group;

$R^{22}$ represents a $C_{1-4}$alkyl or phenyl group;

q represents an integer from 0 to 3;

r represents 2 or 3; and t represents 1 or 2.

The compounds have a stimulant action at $\beta_2$-adrenoreceptors and may be used in the treatment of diseases associated with reversible airways obstruction such as asthma and chronic bronchitis.

4 Claims, No Drawings

ETHANOLAMINE DERIVATIVES

This invention relates to novel ethanolamine derivatives having a stimulant action at $\beta_2$-adrenoreceptors, to processes for their preparation, to pharmaceutical compositions containing them and to their use in medicine.

Ethanolamine derivatives have previously been described as bronchodilators having stimulant activity at $\beta$-adrenoreceptors.

Thus, for example, UK Patent Specification No. 2140800A describes phenethanolamine compounds of the general structure

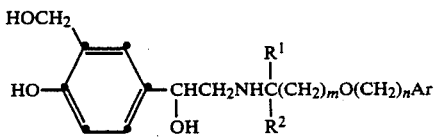

in which $R^1$ and $R^2$ each represent hydrogen or $C_{1-3}$alkyl; m is an integer 2 to 8; n is an integer 1 to 7; and Ar is an optionally substituted phenyl group.

UK Patent Specification No. 2162842A and European Patent Specification No. 0178919A describes aminophenol compounds of the general structure

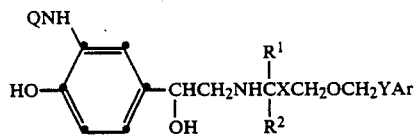

in which $R^1$ and $R^2$ each represented hydrogen of $C_{1-3}$alkyl; X represents a $C_{1-7}$alkylene, $C_{2-7}$alkenylene or $C_{2-7}$alkynylene chain; Y represents a $C_{1-6}$alkylene, $C_{2-6}$alkenylene or $C_{2-6}$alkynylene chain; Ar represents a phenyl group optionally substituted by one or more of a variety of specific substituents; and Q represents a group $R^3CO-$, $R^3NHCO-$, $R^3R^4NSO_2-$, $R^5SO_2-$ where $R^3$ and $R^4$ each represent a hydrogen atom or a $C_{1-3}$alkyl group, and $R^5$ represents a $C_{1-4}$alkyl group.

UK Patent Specification No. 2165542A describes dichloroaniline derivatives of the general structure

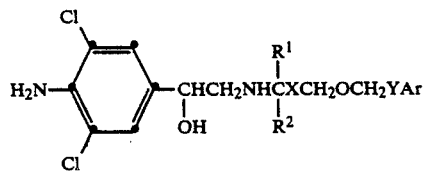

in which $R^1$ and $R^2$ each represent hydrogen or $C_{1-3}$alkyl, X represents a $C_{1-6}$alkylene, $C_{2-6}$alkenylene or $C_{2-6}$alkynylene chain; Y represents a $C_{1-4}$alkylene, $C_{2-4}$alkenylene or $C_{2-4}$alkynylene chain; and Ar represent a phenyl group substituted by one or more of a variety of specific substituents.

We have now found a novel group of compounds which differ structurally from those of UK Patent Specification Nos. 2140800A, 2162842A and 2165542A, and European Patent Specification No. 0178919A, and which have a desirable and useful profile of activity.

Thus the present invention provides compounds of the general formula (I):

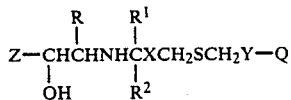

and physiologically acceptable salts and solvates (e.g. hydrates) thereof, wherein
Z represents the group

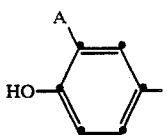 (a)

where A represents a group selected from $HOR^3-$, $R^6NH(CH_2)p-$, $R^{10}R^{11}N-$, $R^{12}OCH_2-$, $CH_3SO_2CH_2-$ or $NCCH_2-$;
where $R^3$ is a $C_{1-3}$alkylene group,
$R^6$ is a group selected from $R^7CO-$, $R^7NHCO-$, $R^7R^8NSO_2-$ or $R^9SO_2-$, and p is zero or 1,
$R^7$ and $R^8$ each represent a hydrogen atom or a $C_{1-3}$alkyl group,
$R^9$ is a $C_{1-3}$alkyl group,
$R^{10}$ and $R^{11}$ each represent a hydrogen atom or a $C_{1-4}$alkyl group or,
when $R^{10}$ is a hydrogen atom, $R^{11}$ may also be a $C_{1-4}$alkoxycarbonyl group, and
$R^{12}$ is a $C_{1-3}$alkyl group;

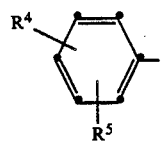 (b)

where one of $R^4$ and $R^5$ is a hydroxy group and the other is a hydrogen or halogen atom or a hydroxy group;

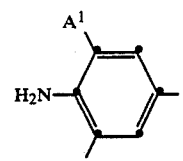 (c)

where $A^1$ is either a chlorine atom or a $-CF_3$ group;

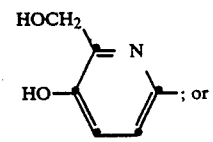 (d)

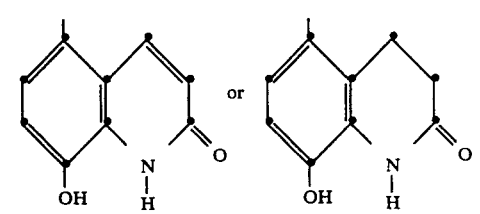 (e)

X represents a bond or a $C_{1-7}$alkylene, $C_{2-7}$alkenylene or $C_{2-7}$alkynylene chain, and Y represents a bond, or a $C_{1-6}$alkylene, $C_{2-6}$alkenylene or $C_{2-6}$alkynylene chain, with the proviso that the sum total of carbon atoms in X and Y is 2 to 10;

R represents a hydrogen atom or a $C_{1-3}$alkyl group;

$R^1$ and $R^2$ each represents a hydrogen atom or a $C_{1-3}$alkyl group with the proviso that the sum total of carbon atoms in $R^1$ and $R^2$ is not more than 4;

Q represents a pyridyl group optionally substituted by one or two substituents selected from halogen atoms or hydroxy, $C_{1-3}$alkyl or $C_{1-3}$alkoxy groups, or Q represents a phenyl group optionally substituted by one or more substituents selected from halogen atoms or the groups $C_{1-6}$alkyl, nitro, $-(CH_2)_qR^{13}$ or $-O(CH_2)_rR^{14}$, or Q represents a phenyl group substituted by an alkylenedioxy group of formula $-O(CH_2)_tO-$; where $R^{13}$ represents hydroxy, $C_{1-6}$alkoxy, cyano, $-NR^{15}R^{16}$, $-NR^{17}COR^{18}$, $-NR^{17}SO_2R^{19}$, $-COR^{20}$, $-SR^{21}$, $-SOR^{22}$ or $-SO_2R^{22}$;

$R^{14}$ represents hydroxy or $C_{1-4}$alkoxy;

$R^{15}$ and $R^{16}$ each represent a hydrogen atom or a $C_{1-4}$alkyl group or $-NR^{15}R^{16}$ forms a saturated heterocyclic amino group which has 5-7 ring members and optionally contains in the ring one or more atoms selected from $-O-$ or $-S-$ or a group $-NH-$ or $-N(CH_3)-$;

$R^{17}$ represents a hydrogen atom or a $C_{1-4}$alkyl group;

$R^{18}$ represents a hydrogen atom or a $C_{1-4}$alkyl, $C_{1-4}$alkoxy, phenyl or $-NR^{15}R^{16}$ group;

$R^{19}$ represents $C_{1-4}$alkyl, phenyl or $-NR^{15}R^{16}$;

$R^{20}$ represents hydroxy, $C_{1-4}$alkoxy or $-NR^{15}R^{16}$;

$R^{21}$ represents a hydrogen atom or a $C_{1-4}$alkyl or phenyl group;

$R^{22}$ represents a $C_{1-4}$alkyl or phenyl group;

q represents an integer from 0 to 3;

r represents 2 or 3; and t represents 1 or 2.

It will be appreciated that the compounds of general formula (I) possess one or more asymmetric carbon atoms. The compounds according to the invention thus include all enantiomers, diastereoisomers and mixtures thereof, including racemates. Compounds in which the carbon atom in the $$-\underset{\underset{OH}{|}}{CH}-$$

group is in the R configuration are preferred.

In the definition of general formula (I), the term alkenylene includes both cis and trans structures.

In the general formula (I), the chain X may be for example a bond, $-CH_2-$, $-(CH_2)_2-$, $-(CH_2)_3-$, $-(CH_2)_4-$, $-(CH_2)_5-$, $-CH_2C\equiv C-$, $-(CH_2)_2CH=CH-$, $-(CH_2)_2C\equiv C-$, $-CH=CHCH_2-$, $-CH=CH(CH_2)_2-$ or $-CH_2C\equiv CCH_2-$. The chain Y may be for example a bond, $-CH_2-$, $-(CH_2)_2-$, $-(CH_2)_3-$, $-(CH_2)_4-$, $-(CH_2)_5-$, $-(CH_2)_6-$, $-CH=CH-$, $-C\equiv C-$, $-CH_2CH=CH-$ or $CH_2C\equiv C-$.

The total number of carbon atoms in the chains X and Y is preferably 4 to 10 inclusive and may be for example, 5, 6, 7 or 8. Compounds wherein the sum total of carbon atoms in the chains X and Y is 5, 6 or 7 are particularly preferred.

One preferred group of compounds of formula (I) is that in which X represents a $C_{3-4}$alkylene chain and Y represents a $C_{1-3}$alkylene chain. Particular compounds of this type are those wherein X represents $-(CH_2)_4-$ and Y represents $-CH_2-$ or $-(CH_2)_3-$.

In the compounds of formula (I) R, $R^1$ and $R^2$ may each be for example methyl, ethyl, propyl or isopropyl groups. If one of $R^1$ and $R^2$ is a propyl or isopropyl group, the other is a hydrogen atom or a methyl group. R, $R^1$ and $R^2$ are each preferably a hydrogen atom or a methyl group.

A preferred group of compounds is that wherein R represents a hydrogen atom.

Another preferred group of compounds is that wherein $R^1$ and $R^2$ are both hydrogen atoms, or $R^1$ is a hydrogen atom and $R^2$ is a $C_{1-3}$alkyl group, particularly a methyl group, or $R^1$ is a methyl group and $R^2$ is a methyl group.

In the definition of Z in compounds of formula (I), $R^3$ may be, for example, $-CH_2-$, $$-\underset{\underset{CH_3}{|}}{CH}-,$$

$-(CH_2)_2-$ or $-(CH_2)_3-$. "Halogen" in the definition of $R^4$ or $R^5$ may be for example chlorine or fluorine. $R^7$, $R^8$, $R^{10}$ and $R^{11}$ may each be, for example, a hydrogen atom or a methyl, ethyl, propyl or isopropyl group. $R^9$ may be for example a methyl, ethyl, propyl or isopropyl group. $R^{12}$ may be for example a methyl, ethyl or propyl group.

Z in compounds of formula (I) may be for example

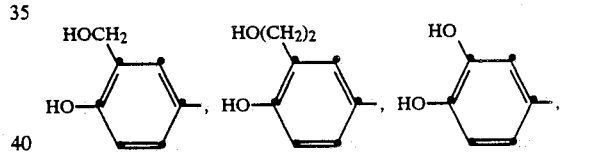

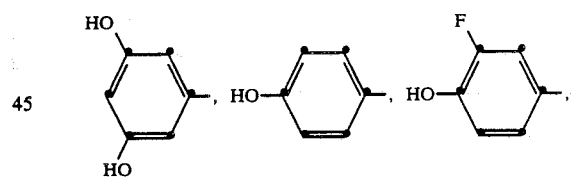

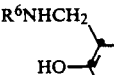

(where $R^6$ is HCO—, $CH_3CO-$, $NH_2CO-$, $(CH_3)_2NSO_2-$ or $CH_3SO_2-$), 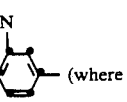 (where $R^6$ is as just defined),

 (where $R^{10}$ is hydrogen and $R^{11}$ is methyl),

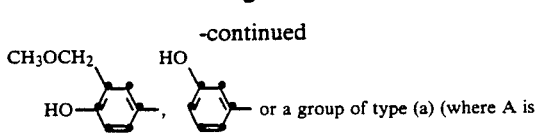, or a group of type (a) (where A is $CH_3SO_2CH_2-$ or $NCCH_2-$) or of type (c), (d) or (e).

The group Z preferably represents

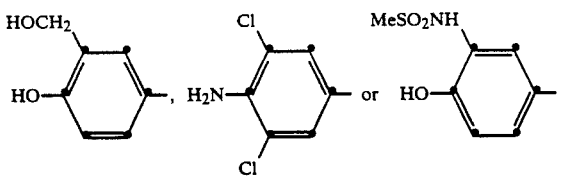

When $-NR^{15}R^{16}$ in compounds of formula (I) represents a saturated heterocyclic group, this may be for example a pyrrolidino, piperidino, hexamethylenimino, piperazino, N-methylpiperazino, morpholino, homomorpholino or thiamorpholino group.

In the compounds of formula (I) Q may be for example an unsubstituted pyridyl or phenyl group.

When Q represents an optionally substituted pyridyl group, this may be attached to the rest of the molecule at either the 2-, 3- or 4-position. When the pyridyl group is substituted, the substituent(s) may be at the 2-, 3-, 4-, 5- or 6-position(s) in the ring.

When Q represents a substituted phenyl group, this may contain one, two or three substituents, which may be present at the 2-, 3-, 4-, 5- or 6-positions on the phenyl ring.

Examples of the optional substituents which may be present on the phenyl group represented by Q include chlorine, bromine, iodine, fluorine, methyl, ethyl, ethoxy, $-(CH_2)_qR^{13}$ [where $R^{13}$ is hydroxy, methoxy, amino, methylamino, ethylamino, dimethylamino, diethylamino, morpholino, pyrrolidino, piperidino, piperazino, N-methylpiperazino, $-NHCOR^{18}$ (where $R^{18}$ is hydrogen or $C_{1-4}$alkyl (e.g. methyl, ethyl, isopropyl or n-butyl), $C_{1-4}$alkoxy (e.g. methoxy, ethoxy, isopropoxy or n-butoxy), phenyl, amino or N,N-dimethylamino), $-N(CH_3)COCH_3$, $-NR^{17}SO_2R^{19}$, (where $R^{17}$ represents a hydrogen atom or a methyl group and $R^{19}$ represents methyl, butyl, phenyl, amino or dimethylamino), $-COOH$, $-COOCH_3$, $-COOCH_2CH_2CH_3$, $-CONH_2$, $-CON(CH_3)_2$, $-CON(CH_2CH_3)_2$, $-CON(CH_2CH_2CH_3)_2$,

$-SR^{21}$ (where $R^{21}$ is methyl, ethyl or phenyl) $-SOCH_3$, $-SO_2CH_3$, or CN, and q is zero, 1, 2 or 3], $-NO_2$, $-O(CH_2)_2OH$, $-O(CH_2)_3OH$, $-O(CH_2)_2OCH_3$, or $-O(CH_2)_2OCH_2CH_3$.

A particularly preferred group of compounds of formula (I) is that in which Q represents a pyridyl group, or Q represents a phenyl group optionally substituted by the group $-CON(CH_2CH_3)_2$.

Preferred compounds according to the invention are 4-hydroxy-α¹-[[[6-[(2-phenylethyl)thio]hexyl]amino]methyl]-1,3-benzenedimethanol;

4-amino-3,5-dichloro-α-[[[6-[[2-(2-pyridinyl)ethyl]thio]hexyl]amino]methyl]benzenemethanol;
N,N-diethyl-4-[4-[[6-[[2-hydroxy-2-[4-hydroxy-3-[(methanesulphonyl) amino]phenyl]ethyl]amino]hexyl]thio]butyl]benzamide;
and their physiologically acceptable salts and solvates.

Suitable physiologically acceptable salts of the compounds of general formula (I) include acid addition salts derived from inorganic and organic acids, such as hydrochlorides, hydrobromides, sulphates, phosphates, maleates, tartrates, citrates, benzoates, 4-methoxybenzoates, 2- or 4-hydroxybenzoates, 4-chlorobenzoates, p-toluenesulphonates, naphthalenesulphonates, methanesulphonates, sulphamates, ascorbates, salicylates, acetates, diphenylacetates, triphenylacetates, adipates, fumarates, succinates, lactates, glutarates, gluconates, tricarballylates, hydroxynaphthalenecarboxylates e.g. 1-hydroxy- or 3-hydroxy-2-naphthalenecarboxylates, or oleates. The compounds may also form salts with suitable bases. Examples of such salts are alkali metal (e.g. sodium and potassium) and alkaline earth metal (e.g. calcium or magnesium) salts, and salts with organic bases (e.g. triethylamine).

The compounds according to the invention have a selective stimulant action at $\beta_2$-adrenoreceptors, which furthermore is of a particularly advantageous profile. The stimulant action was demonstrated in the isolated trachea of the guinea-pig, where compounds were shown to cause relaxation of contractions induced by $PGF_{2\alpha}$ or electrical stimulation. Compounds according to the invention have shown a particularly long duration of action in these tests.

The compounds according to the invention may be used in the treatment of diseases associated with reversible airways obstruction such as asthma and chronic bronchitis.

The compounds according to the invention may also be used for the treatment of premature labour, depression and congestive heart failure, and are also indicated as useful for the treatment of inflammatory and allergic skin diseases, glaucoma, and in the treatment of conditions in which there is an advantage in lowering gastric acidity, particularly in gastric and peptic ulceration.

The invention accordingly further provides compounds of formula (I) and their physiologically acceptable salts and solvates for use in the therapy or prophylaxis of diseases associated with reversible airways obstruction in human or animal subjects.

The compounds according to the invention may be formulated for administration in any convenient way. The invention therefore includes within its scope pharmaceutical compositions comprising at least one compound of formula (I) or a physiologically acceptable salt or solvate thereof formulated for use in human or veterinary medicine. Such compositions may be presented for use with physiologically acceptable carriers or excipients, optionally with supplementary medicinal agents.

The compounds may be formulated in a form suitable for administration by inhalation or insufflation, or for oral, buccal, parenteral, topical (including nasal) or rectal administration. Administration by inhalation or insufflation is preferred.

For administration by inhalation the compounds according to the invention are conveniently delivered in the form of an aerosol spray presentation from pressurised packs, with the use of a suitable propellant, such as dichlorodifluoromethane, trichlorofluoromethane, dichlorotetrafluoroethane, carbon dioxide or other suitable gas, or from a nebuliser. In the case of a pressurised aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in for example capsules or cartridges of e.g. gelatin, or blister packs from which the powder may be administered with the aid of an inhaler or insufflator.

For oral administration, the pharmaceutical composition may take the form of, for example, tablets, capsules, powders, solutions, syrups or suspensions prepared by conventional means with acceptable excipients.

For buccal administration the composition may take the form of tablets, drops or lozenges formulated in conventional manner.

The compounds of the invention may be formulated for parenteral administration by bolus injection or continuous infusion. Formulations for injection may be presented in unit dosage form in ampoules, or in multidose containers with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for reconstitution with a suitable vehicle, e.g. sterile pyrogen-free water, before use.

For topical administration the pharmaceutical composition may take the form of ointments, lotions or creams formulated in a conventional manner, with for example an aqueous or oily base, generally with the addition of suitable thickening agents and/or solvents. For nasal application, the composition may take the form of a spray, formulated for example as an aqueous solution or suspension or as an aerosol with the use of a suitable propellant.

The compounds of the invention may also be formulated in rectal compositions such as suppositories or retention enemas, e.g. containing conventional suppository bases such as cocoa butter or other glyceride.

Where pharmaceutical compositions are described above for oral, buccal, rectal or topical administration, these may be presented in a conventional manner associated with controlled release forms.

A proposed daily dosage of active compound for the treatment of man is 0.005 mg to 100 mg, which may be conveniently administered in one or two doses. The precise dose employed will of course depend on the age and condition of the patient and on the route of administration. Thus a suitable dose for administration by inhalation is 0.005 mg to 20 mg, for oral administration is 0.02 mg to 100 mg, and for parenteral administration is 0.01 mg to 2 mg for administration by bolus injection and 0.01 mg to 25 mg for administration by infusion.

In the following description relating to the preparation of compounds of formula (I) and intermediates used in the preparation thereof, Z, R, $R^1$, $R^2$, X, Y and Q are as defined for general formula (I) unless otherwise specified. Any hydroxy and/or amino groups present in the starting materials may need to be in a protected form and the final step may be the removal of a protecting group. Suitable protecting groups and methods for their removal are for example those described in "Protective Groups in Organic Chemistry", Ed. J. F. W. McOmie (Plenum Press, 1973). Thus hydroxyl groups may for example be protected by acyl groups such as acetyl, or as tetrahyropyranyl derivatives. Suitable amino protecting groups include acyl groups such as acetyl, trichloroacetyl or trifluoroacetyl. Conventional methods of deprotection may be used. Thus for example tetrahydropyranyl groups may be cleaved by hydrolysis under acidic conditions. Acyl groups may be removed by hydrolysis with a base such as sodium hydroxide or potassium carbonate, or a group such as trichloroacetyl may be removed by reduction with, for example, zinc and acetic acid.

In one general process (1), a compound of general formula (I) may be prepared by alkylation, using conventional alkylation procedures.

Thus, for example, in one process (a), a compound of general formula (I) in which $R^1$ is a hydrogen atom may be prepared by alkylation of an amine of general formula (II)

followed where necessary by removal of any protecting groups.

The alkylation (a) may be effected using an alkylating agent of general formula (III):

(wherein L represents a leaving group, for example a halogen atom such as chlorine, bromine or iodine, or a hydrocarbylsulphonyloxy group such as methanesulphonyloxy or p-toluenesulphonyloxy).

The alkylation is preferably effected in the presence of a suitable acid scavenger, for example, inorganic bases such as sodium or potassium carbonate, organic bases such as triethylamine, diisopropylethylamine or pyridine, or alkylene oxides such as ethylene oxide or propylene oxide. The reaction is conveniently effected in a solvent such as acetonitrile or an ether e.g. tetrahydrofuran or dioxan, a ketone e.g. butanone or methyl isobutyl ketone, a substituted amide e.g. dimethylformamide or a chlorinated hydrocarbon e.g. chloroform at a temperature between ambient and the reflux temperature of the solvent.

According to another example (b) of an alkylation process, a compound of general formula (I) in which $R^1$ represents a hydrogen atom may be prepared by alkylation of an amine of general formula (II) with a compound of general formula (IV):

in the presence of a reducing agent, followed where necessary by removal of any protecting groups.

Suitable reducing agents include a hydride such as diborane or a metal hydride such as sodium borohydride, sodium cyanoborohydride or lithium aluminium hydride. Suitable solvents for the reaction with these reducing agents will depend on the particular hydride used, but will include alcohols such as methanol or ethanol, or ethers such as diethyl ether or tert-butyl methyl ether, or tetrahydrofuran.

Alkylation of an amine (II) with a compound of formula (IV) may result in formation of the intermediate imine of formula (V)

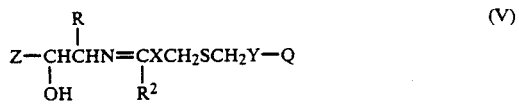

Reduction of the imine using the conditions described above, gives a compound of general formula (I).

In another general process (2), a compound of general formula (I) may be prepared by reduction. Thus, for example, a compound of general formula (I) may be prepared by reducing an intermediate of general formula (VI):

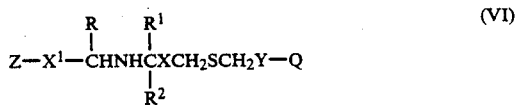

(wherein $X^1$ represents a reducible group and/or Z and/or Q contains a reducible group and the other(s) take the appropriate meaning as follows, which is $X^1$ is —CH(OH)— and Z and Q are as defined in formula (I)), followed where necessary by removal of any protecting groups.

Suitable reducible groups include those wherein $X^1$ is a group >C=O, and Z and/or Q contains a substituent —CHO or —$CO_2R^{23}$ (where $R^{23}$ represents a hydrogen atom or an alkyl (e.g. $C_{1-3}$ alkyl) group).

The reduction may be effected using reducing agents conveniently employed for the reduction of carboxylic acids, aldehydes, esters and ketones.

Thus for example when $X^1$ in general formula (VI) represents a >C=O group and/or Z and/or Q contains a substituent —CHO or —$CO_2R^{23}$ this may be reduced to a —CH(OH)— or —$CH_2OH$ group respectively using for example, a complex metal hydride such as lithium aluminium hydride. The reaction may be effected in a solvent such as an ether e.g. diethyl ether or tetrahydrofuran, or a halogenated hydrocarbon e.g. dichloromethane, at a temperature of 0° C. to the reflux temperature of the solvent.

In the general processes described above, the compound of formula (I) obtained may be in the form of a salt, conveniently in the form of a physiologically acceptable salt. Where desired, such salts may be converted to the corresponding free acids using conventional methods.

Physiologically acceptable salts of the compounds of general formula (I) may be prepared by reacting a compound of general formula (I) with an appropriate acid or base in the presence of a suitable solvent such as acetonitrile, acetone, chloroform, ethyl acetate or an alcohol, e.g. methanol, ethanol or isopropanol.

Physiologically acceptable salts may also be prepared from other salts, including other physiologically acceptable salts, of the compounds of general formula (I), using conventional methods.

When a specific enantiomer of a compound of general formula (I) is required, this may be obtained by resolution of a corresponding racemate of a compound of general formula (I) using conventional methods.

Thus, in one example an appropriate optically active acid may be used to form salts with the racemate of a compound of general formula (I). The resulting mixture of isomeric salts may be separated for example by fractional crystallisation, into the diastereoisomeric salts from which the required enantiomer of a compound of general formula (I) may be isolated by conversion into the required free base.

Alternatively, enantiomers of a compound of general formula (I) may be synthesised from the appropriate optically active intermediates using any of the general processes described herein.

Specific diastereoisomers of a compound of formula (I) may be obtained by conventional methods for example, by synthesis from an appropriate asymmetric starting material using any of the processes described herein, or by conversion of a mixture of isomers of a compound of general formula (I) into appropriate diastereoisomeric derivatives e.g. salts which then can be separated by conventional means e.g. by fractional crystallisation.

The intermediate compounds of general formula (VI) in which $X^1$ represents a group >C=O may be prepared from a haloketone of formula (VII):

(where Hal represents a halogen atom, and any hydroxyl and/or amino group(s) in the group Z may optionally be protected) by reaction with an amine of general formula (VIII)

The reaction may be effected in a cold or hot solvent, for example dimethylformamide or an ester such as ethyl acetate, in the presence of a base such as diisopropylethylamine.

Intermediates of formula (III) may be prepared by methods analogous to these used for the preparation of known compounds such as are described in UK Patent Specification No. 2140800A.

Alternatively, intermediates for formula (III) may be prepared by hydrolysis of a thiol ester of formula (IX)

(wherein $R^{24}$ is an alkyl group and Y and Q are as previously defined), using a suitable base such as potassium carbonate or sodium hydroxide, in a solvent such as an alcohol, for example, methanol at normal or elevated temperature.

The compounds of formula (IX) may be prepared from the reaction of a compound of formula (X)

(wherein Y and Q are as previously defined, and L is a leaving group such as a hydrocarbylsulphonyloxy group, for example, methanesulphonyloxy or p-toluenesulphonyloxy) with a thiol acid of formula (XI)

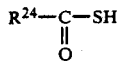

(wherein $R^{24}$ is as defined above). Such a reaction is preferably carried out in the presence of a weak base such as potassium carbonate and in a suitable solvent such as dimethyl sulphoxide. The reaction is conveniently effected at a temperature in the range of 0° to 100° C., preferably between 20° and 50° C.

The compounds of formula (X) can be prepared from their corresponding alcohols, of formula (XII)

(wherein Y and Q are as previously defined) by any standard conversion of a hydroxyl group to the group L, which are well known in the art.

The amines of formula (II) and haloketones of formula (VII) and thiol acids of formula (XI) are either known compounds or may be prepared by methods analogous to those used for the preparation of the known compounds.

Intermediates of formulae (IV) and (VIII) may be prepared by methods analogous to those used for the preparation of known compounds. Suitable methods include those described in UK Patent Specification Nos. 2140800A and 2159151A and in the exemplification included hereinafter.

The following examples illustrate the invention. Temperatures are in °C. 'Dried' refers to drying using magnesium sulphate or sodium sulphate. Thin layer chromatography (t.l.c.) was carried out over silica. Flash column chromatography (FCC) was carried out on silica (Merck 9385) unless otherwise stated. The following abbreviations are used: DEA- N,N-diisopropylethylamine; DMF-dimethylformamide; DMSO-dimethylsulphoxide; TAB - tetra-n-butylammonium hydrogen sulphate; BTPC- bis(triphenylphosphine)palladium (II) chloride; System A - toluene/ethanol/0.88 ammonia.

Intermediate 1

[2-[(6-Bromohexyl)thio]ethyl]benzene

A mixture of 1,6-dibromohexane (20 g), 2-phenylethanethiol (4 g), 50% sodium hydroxide (25 ml) and TAB (1 g) was vigorously stirred at 23° for 18 h. The mixture was diluted with water (150 ml), extracted with ether (2×100 ml) and the extract was washed with water (2×100 ml), brine (50 ml), dried and evaporated in vacuo to give a colourless oil (24 g). Purification by FCC eluting with cyclohexane followed by cyclohexane-ether (9:1) afforded the title compound as a colourless oil (5.2 g), t.l.c. (cyclohexane-ether 9:1) Rf 0.28.

Intermediate 2

2-[2-[(Bromohexyl)thio]ethyl]pyridine

A mixture of 2-pyridineethanethiol (500 mg), 1,6-dibromohexane (1.7 ml), 50% w/v sodium hydroxide (5 ml) and TAB (200 mg) was stirred vigorously for 3 h, diluted with water (50 ml) and extracted with ethyl acetate (3×50 ml). The combined organic extracts were dried and concentrated to give an oil which was purified by FCC eluting with hexane followed by hexane-ethyl acetate (4:1) to give the title compound as a clear oil (720 mg), t.l.c. (System A 80:20:1) Rf 0.75.

Intermediate 3

[3-[(6-Bromohexyl)thio]propyl]benzene

A mixture of 3-phenylpropylmercaptan (2.0 g), 1,6-dibromohexane (9.6 g), TAB (330 mg), and aqueous sodium hydroxide (50% w/v, 5.1 ml) was stirred at room temperature overnight, diluted with water (50 ml) and extracted with ether (50, 30, 20 ml). The dried extracts were concentrated and purified by FCC eluting with cyclohexane followed by cyclohexane:ether (19:1) to give the title compound as a colourless oil (1.6 g), t.l.c. (hexane:ether 19:1) Rf 0.51.

Intermediate 4

N,N-Diethyl-4-(4-hydroxy-1-butynyl)benzamide

A mixture of N,N-diethyl-4-iodobenzamide (1.0 g), 3-butyn-1-ol (0.26 g), diethylamine (5 ml) and THF (5 ml, distilled from calcium hydride) were stirred at 20° under nitrogen and BTPC (0.05 g) and copper (I) iodide (0.06 g) were added. The resulting yellow solution was stirred under nitrogen for 2.5 h until t.l.c. showed complete consumption of the starting iodoamide (Rf 0.4). The mixture was diluted with ether (50 ml), filtered and concentrated to give a dark oil (1.11 g). The crude product was chromatographed on a column of silica (Merck 9385, 30 g), eluting initially with ether (5×30 ml) and then with ether/ethyl acetate (9:1). The title compound was obtained as a colourless oil which solidified to a white crystalline solid (0.72 g), m.p. 70°–73°.

Intermediate 5

N,N-Diethyl-4-(4-hydroxybutyl)benzamide

A solution of N,N-diethyl-4-(4-hydroxy-1-butynyl)benzamide (10 g), in methanol (100 ml) was hydrogenated over platinum on charcoal (50% aqueous paste, 1.0 g), and palladium oxide (50% aqueous paste, 1.0 g). The reaction mixture was filtered (hyflo) and the solvent was removed by evaporation, followed by azeotropic distillation with toluene (2×50 ml) to leave a pale grey oil (10.60 g). A portion of the product (0.85 g) was purified by chromatography on a column of silica (Merck 7729, 45 g) eluting with ether/methanol (20:1) to give the title compound as a colourless oil (0.8 g), t.l.c. (ether), Rf 0.2.

Intermediate 6

N,N-Diethyl 4-[4-[(methanesulphonyl)oxy]butyl]benzamide

Methanesulphonyl chloride (1.92 ml) was added dropwise to a solution of N,N-diethyl 4-(4-hydroxybutyl)benzamide (4.77 g) and triethylamine (4 ml) in dichloromethane (40 ml) at 0°–5° under a calcium chloride guard tube. After 1 h the solution was washed with 2M sodium carbonate (40 ml), dried and evaporated in vacuo to afford the title compound as a pale yellow oil (6.58 g), t.l.c. (ethylacetate) Rf 0.39.

Intermediate 7

S-[4-[4-[(Diethylamino)carbonyl]phenyl]butyl]ethanethioate

N,N-Diethyl-4-[4-[(methanesulphonyl)oxy]butyl]benzamide (2.0 g) in DMSO (20 ml) was added to a solution of thiolacetic acid (1.0 ml) and potassium carbonate (1.0 g) in DMSO (20 ml). The dark solution was stirred for 17 h at 35°, allowed to cool to room temperature, poured into phosphate buffer (pH 6.5, 200 ml) and extracted with ethyl acetate (2×100 ml). The organic layer was washed with brine (200 ml), dried and evaporated in vacuo. The residual brown oil was purified by FCC eluting with diethyl ether to give the title compound as a brown oil (1.6 g), t.l.c. (ether) Rf 0.50.

Intermediate 8

N,N-Diethyl-4-(4-mercaptobutyl)benzamide

S-[4-[4-[(Diethylamino)carbonyl]phenyl]butyl]ethanethioate (1.6 g) and potassium carbonate (1.4 g) in methanol (20 ml) were stirred under nitrogen for 4 h. Methanol was removed in vacuo and the brown oil partitioned between ether (3×40 ml) and water (40 ml). The ether was removed in vacuo to give the title compound a brown oil (1.58 g crude), t.l.c. (diethyl ether:-hexane; 2:1) Rf 0.38.

Intermediate 9

4-[4-[(6-Bromohexyl)thio]butyl]-N,N-diethylbenzamide

A mixture of N,N-diethyl-4-(4-mercaptobutyl)benzamide (1.54 g crude product from Intermediate 8), 1,6-dibromohexane (16 ml), TAB (136 mg) and 50% aqueous sodium hydroxide solution (2.0 ml) was stirred under nitrogen for 48 h, diluted with water (50 ml) and extracted with diethyl ether (2×50 ml). The organic phase was dried and evaporated in vacuo to give a yellow oil. Purification by FCC eluting with hexane:-diethyl ether (19:1→2:1) gave the title compound as a yellow oil (0.85 g), t.l.c. (hexane:diethyl ether; 1:1) Rf 0.18.

EXAMPLE 1

4-Hydroxy-$\alpha^1$-[[[6-[(2-phenylethyl)thio]hexyl]amino]methyl]-1,3-benzenedimethanol A solution of $\alpha^1$-(aminomethyl)-4-hydroxy-1,3-benzenedimethanol (0.9 g), [2-[(6-bromohexyl)thio]ethyl]-benzene (1 g) and DEA (0.77 g) in DMF (10 ml) was heated at 75° for 2 h. The mixture was diluted with water (100 ml), acidified to pH 5 with 2M hydrochloric acid, basified to pH 8 with sodium bicarbonate and extracted with ethyl acetate (2×50 ml). The extract was washed with water (20 ml) and brine (20 ml), dried and evaporated in vacuo to give an oil which was purified by FCC on triethylamine deactivated silica using ethyl acetate - methanol (17:3) as the eluant to give a yellow oil. Trituration with ether afforded the title compound as a pale yellow solid (0.32 g) m.p. 75°-77°.

Analysis Found: C,68.0; H,8.5; N,3.5. $C_{23}H_{33}NO_3S$ requires C,68.4; H,8.2; N,3.5%.

EXAMPLE 2

4-Amino-3,5-dichloro-$\alpha$-[[[6-[[2-(2-pyridinyl)ethyl]thio]hexyl]amino]methyl]benzenemethanol A solution of 2-[2-[(6-bromohexyl)thio]ethyl]pyridine (2 g), 4-amino-$\alpha$-(aminomethyl)-3,5-dichlorobenzenemethanol (2.2 g), and DEA (1 g) in DMF (15 ml) was heated at 100° for 2.5 h. The solvent was evaporated in vacuo and the resulting oil was purified by FCC eluting with toluene-ethanol-triethylamine (99:1:1→95:5:1) to give a yellow oil which was triturated under hexane-ether (2:1) to give the title compound as a white solid (1.4 g) m.p. 83°-84°.

Analysis Found: C,57.0; H,6.6; N,9.3; Cl,16.3; S,7.2. $C_{21}H_{29}Cl_2N_3OS$ requires C,57.0; H,6.6; N,9.5; Cl,16.0, S,7.2%.

EXAMPLE 3

N-[2-Hydroxy-5-[1-hydroxy-2-[[6-[(3-phenylpropyl)thio]hexyl]amino]ethyl]phenyl]methanesulphonamide benzoate salt A solution of N-[5-(2-amino-1-hydroxyethyl)-2-hydroxyphenyl]methanesulphonamide (1.82 g), [3-[(6-bromohexyl)thio]propyl]benzene (1.55 g) and DEA (0.7 g) in DMF (30 ml) was stirred at 80° for 2.5 h. The solvent was evaporated and the residue was purified by FCC eluting with System A (80:2:2) to give a white solid which was dissolved in methanol (6 ml) and partitioned between 8% sodium bicarbonate solution (50 ml) and ethyl acetate (2×50 ml). The combined dried organic extracts were evaporated to an orange oil, which was dissolved in methanol (5 ml) and benzoic acid (130 mg) was added. The solvent was evaporated and the residue triturated under ether to give the title compound as a white solid (570 mg), m.p. 127°-128°.

Analysis Found: C,61.2; H,7.3; N,4.6; S,10.5. $C_{24}H_{36}N_2O_4S_2 \cdot C_6H_5CO_2H \cdot \frac{1}{4}H_2O$ requires C,61.3; H,7.1; N,4.6; S,10.6%.

EXAMPLE 4

N,N-Diethyl-4-[4-[[6-[[2-hydroxy-2-[4-hydroxy-3-[(methanesulphonyl)amino]phenyl]ethyl]amino]hexyl]thio]-butyl]benzamide A solution of 4-[4-[(6-bromohexyl)thio]butyl]-N,N-diethylbenzamide (863 mg), N-[5-(2-amino-1-hydroxyethyl)-2-hydroxyphenyl]methane sulphonamide (1.21 g) and DEA (0.42 ml) in DMF (20 ml) was stirred at 80°-90°, under nitrogen, for 8 h. The solution was allowed to cool and DMF removed in vacuo to give a brown oil. Purification by FCC eluting with System A (80:20:1) gave the title compound as a brown oil (0.62 g). A solution of the oil (404 mg) and 4,4'-methylenebis(3-hydroxy-2-naphthalene carboxylic acid) (132 mg) in methanol (40 ml) was refluxed for 18 h. The mixture was filtered and the filtrate evaporated to give a gum which, when triturated with dry ether, afforded the embonate salt of the title compound as a brown foam. The foam was dissolved in methanol (2 ml) and partitioned between sodium bicarbonate (20 ml) and ethyl acetate (3×20 ml). The organic phase was dried and evaporated in vacuo to give the title compound as a brown solid (210 mg), m.p. 51°-53°.

Analysis Found: C,58.7; H,8.0; N,6.4; S,9.9. $C_{30}H_{47}N_3O_5S_2 \cdot 1.2H_2O$ requires C,58.5; H,8.1; N,6.8; S,10.4%.

The following are examples of suitable formulations of compounds of the invention. The term 'active ingredient' is used herein to represent a compound of the invention.

| Tablets (Direct Compression) | |
|---|---|
| | mg/tablet |
| Active ingredient | 2.0 |
| Microcrystalline cellulose USP | 196.5 |
| Magnesium Stearate BP | 1.5 |
| Compression Weight | 200.0 |

The active ingredient is sieved through a suitable sieve, blended with the excipients and compressed using 7 mm diameter punches.

Tablets of other strengths may be prepared by altering the ratio of active ingredient to microcrystalline cellulose or the compression weight and using punches to suit.

The tablets may be film coated with suitable film forming materials, such as hydroxypropylmethylcellulose, using standard techniques. Alternatively, the tablets may be sugar coated.

| Metered Dose Pressurised Aerosol (Suspension Aerosol) | | |
|---|---|---|
| Active ingrediant | mg/metered dose | Per can |
| micronisd | 0.100 | 26.40 mg |
| Oleic Acid BP | 0.010 | 2.64 mg |
| Trichlorofluoromethane BP | 23.64 | 5.67 g |
| Dichlorodifluoromethane BP | 61.25 | 14.70 g |

The active ingredient is micronised in a fluid energy mill to a fine particle size range. The oleic acid is mixed with the trichlorofluoromethane at a temperature of 10°–15° C. and the micronised drug is mixed into the solution with a high shear mixer. The suspension is metered into aluminium aerosol cans and suitable metering valves delivering 85 mg of suspension are crimped onto the cans and the dichlorodifluoromethane is pressure filled into the cans through the valves.

| Inhalation Cartridges | |
|---|---|
| | mg/cartridge |
| Active ingredient micronised | 0.200 |
| Lactose BP to | 25.0 |

The active ingredient is micronised in a fluid energy mill to a fine particle size range prior to blending with normal tabletting grade lactose in a high energy mixer. The powder blend is filled into No. 3 hard gelatin capsules on a suitable encapsulating machine. The contents in the cartridges are administered using a powder inhaler such as the Glaxo Rotahaler.

We claim:

1. A compound of formula (I)

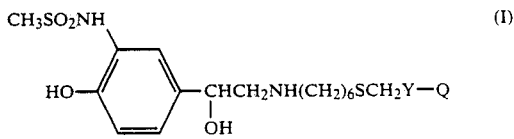

or a physiologically acceptable salt or solvate thereof, wherein
   Y represents a $C_{1-3}$ alkylene chain,
   Q represents a phenyl group, optionally substituted by $-CONR^{15}R^{16}$, and
   $R^{15}$ and $R^{16}$ each represent a hydrogen atom or a $C_{1-4}$ alkyl group.

2. N-[2-Hydroxy-5-[1-hydroxy-2-[[6-(3-phenyl propyl)thio]hexyl]amino]ethyl]phenyl]methanesulphonamide; or a physiologically acceptable salt or solvate thereof.

3. N,N-Diethyl-4-[4-[[6-[[2-hydroxy-2-[4-hydroxy-3-[(methanesulphonyl)amino]phenyl]ethyl]amino]hexyl]thio]butyl]benzamide; or a physiologically acceptable salt or solvate thereof.

4. A pharmaceutical composition for therapy or prophylaxis of a disease associated with reversible airways obstruction such as asthma or chronic bronchitis, which comprises an effective amount to alleviate said disease of at least one compound of formula (I) as defined in claim 1 or a physiologically acceptable salt or solvate thereof, together with a physiologically acceptable carrier or excipient.

* * * * *